(12) United States Patent
Sembo

(10) Patent No.: US 6,346,261 B1
(45) Date of Patent: Feb. 12, 2002

(54) PESTICIDAL COMPOSITION

(75) Inventor: Satoshi Sembo, Takarazuka (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/119,784

(22) Filed: Jul. 21, 1998

(30) Foreign Application Priority Data

Oct. 7, 1997 (JP) .............................................. 9-274364

(51) Int. Cl.[7] .......................... A01N 25/00; A01N 25/36
(52) U.S. Cl. ........................ 424/405; 426/403; 514/919
(58) Field of Search ................................ 424/405, 403; 514/919

(56) References Cited

U.S. PATENT DOCUMENTS

| | | | | |
|---|---|---|---|---|
| 4,594,380 A | * | 6/1986 | Chapin et al. ............... | 524/144 |
| 4,985,251 A | * | 1/1991 | Levy et al. ................. | 424/404 |
| 5,130,136 A | | 7/1992 | Shono et al. ................ | 424/405 |
| 5,698,209 A | * | 12/1997 | Shono et al. ................ | 424/405 |

OTHER PUBLICATIONS

Database CaPlus, DN 102:57742: Ishaaya, I. Phytoparasitica, 12(2), 99–108, Feb. 1984.*
Database CaPlus, DN 115:44178: Follett, P. A. J. Entomol. Sci. 25(3), 357–365, Mar. 1990.*
Database CaPlus, DN 110:22688: Kumar, S. Environ. Pollut. 57(4), 275–280, Apr. 1989.*
Database CaPlus, DN 128:305105; Guerrini, V. et al. Vet. Parasitol. 74, 289–297, Feb. 1998.*
European Search Report dated Feb. 2, 1999.

* cited by examiner

*Primary Examiner*—Michael Borin
(74) *Attorney, Agent, or Firm*—Stevens, Davis, Miller & Mosher, L.L.P.

(57) ABSTRACT

A pesticidal composition which comprises an insect growth regulating compound (for example, pyriproxyfen) and carane-3,4-diol (for example 1S,3S,4S,6R-carane-3,4-diol) as an active ingredient. The pesticidal composition is highly effective for pests, especially flea eggs.

12 Claims, No Drawings

PESTICIDAL COMPOSITION

FIELD OF INVENTION

The present invention relates to a pesticidal composition, especially a pesticidal composition suitable for controlling hatch of flea eggs.

BACKGROUND ART(S)

Carane-3,4-diol is known as an active ingredient of pest repellent in U.S. Pat. No. 5,130,136.

DISCLOSURE OF INVENTION

The object of the present invention is to provide a pesticidal composition suitable for controlling fleas.

According to the present invention, the use of insect growth regulating compound with carane-3,4-diol is much more effective for controlling pests, especially fleas than a sole use of insect growth regulating compound. Therefore, the present invention provides a new use of carane-3,4-diol which was known as an active ingredient.

The insect growth regulating compounds to be used in the present invention include juvenile hormone-like compounds such as pyriproxyfen, methoprene, fenoxycarb, etc.; chitin synthesis inhibition compounds such as chlorfluazuron, hexaflumuron, lufenuron, teflubenzuron, flufenoxuron, N-2,6-difluorobenzoyl-N'-[2-fluoro-4-(1,1,2,3,3,3-hexafluoropropoxy)phenyl]urea and N-2,6-difluorobenzoyl-N'-[2-fluoro-4-(1,1,2,2-tetrafluoroethoxy)phenyl]urea, etc.; and so on.

The weight ratio of an insect growth regulating compound and carane-3,4-diol used in the present invention is usually within the range of 1:3 to 1:5000, preferably 1:10 to 1:1000.

Carane-3,4-diol used in the present invention has various stereoisomers and any active isomers can be used in the present invention. Especially, 1S,3S,4S,6R-carane-3,4-diol, 1R,3R,4R,6S-carane-3,4-diol and the isomers containing thereof in higher amount are used more effectively.

The present pesticidal composition can usually contain suitable carriers, optionally surface active agents and the other auxiliaries for formulation in addition to insect growth regulating compounds and carane-3,4-diol. The present pesticidal composition can be formulated to lotions, spot-on formulations, pour-on formulations, shampoos, dusts, aerosol formulations, collars, ear-tags, and so on.

The carriers used in the present invention include solid carriers such as kaolin clay, diatomaceous earth, bentonite, terra alba, sericite, quartz, talc, silica, ceramics and soon and liquid carriers such as water, alcohols (methanol, ethanol, etc.), ketones (acetone, methyl ethyl ketone, etc.), hydrocarbons (toluene, xylene, kerosene, hexane, paraffin, petroleum benzine, etc.), halogenated hydrocarbons (dichloroethane, trichloroethane, etc.), esters (ethyl acetate, butyl acetate, etc.), ethers (diethyl ether, dioxane, etc.) and so on. In case that the present composition is an aerosol formulation, it includes gaseous carrier such as nitrogen, carbon dioxide, dimethyl ether, LPG, chlorofluorocarbons and so on as a propellant.

In case that the present composition includes surface active agents, typical examples of the used surface active agents are alkylsulfate esters, alkylarylsulfonic acid salts, alkylaryl ether, polyoxyetylenated alkyl aryl ethers, polyoxyetyleneglycol ethers, polyhydric alcohol esters, sugar alcohol derivatives, and so on.

In addition, the other auxiliaries for formulation in the present pesticidal composition include sticking agents and dispersing agents such as casein, gelatin, starch, gum arabic, alginic acid, cellulose derivatives, lignin derivatives, water-soluble synthetic polymers (polyvinyl alcohol, polyvinylpyrrolidone, polyacrylic acids, etc.), and stabilizing agents such as PAP (isopropyl acid phosphate), BHT (dibutylhydroxytoluene, 2,6-di-tert-butyl-4-methylphenol), BHA (butylhydroxyanisol, a mixture of 2-tert-butyl-4-methoxyphenol and 3-tert-butyl-4-methoxyphenol), vegetable oils, mineral oils, aliphatic acids, aliphatic acid esters, and so on.

Moreover, the present pesticidal composition can contain the other pesticidal compound such as pyrethroid compounds (permethrin, phenothrin, cyphenothrin, etc.); organophosphorus compounds (diazinon, dichlorvos, tetrachlorvinphos, etc.); carbamate compounds (propoxur, carbaryl, methoxadiazone, etc.); chloronicotyl compounds (nitenpyram, etc.); phenylpyrazole compounds; and so on.

In case that the present pesticidal composition is formulated to collars or ear-tags, resins such as vinyl chloride, polyurethane, and the like are usually used as their base material. The base material can contain, if necessary, plasticizer such as phthalic acid ester (dimethyl phthalate, dioctyl phthalate, etc.), adipic acid ester, stearic acid, and so on. When the collars or ear-tags are produced, an insect growth regulating compound and carane-3,4-diol may be mixed and kneaded with the base material described above, molded by injection, extrusion, press, and so on, and then formed and/or cut suitably.

The present pesticidal composition is especially effective against fleas such as cat flea (*Ctenocephalides felis*), dog flea (*Ctenocephalides canis*), oriental rat flea (*Xenopsylla cheopis*), human flea(*Pulex irritans*), etc. It is also effective against lice such as *Haematopinus eurysternus, Damalinia ovis,* etc.; acarina such as *Boophilus microplus,* etc.; Diptera such as housefly (*Musca domestics*), *Musca hervei, Musca bezzii, Haematonia irritans, Simulium iwatens, Culicoides oxystoma, Tabanus chrysurus,* common mosquito (*Culex pipiens*), *Aedes albopictus,* Psychodidae, midges (Chironomidae), etc.; Dictyoptera such as German cockroach (*Blattella germanica*), smokybrown cockroach (*Periplaneta fuliginosa*), American cockroach (*Periplaneta americana*),etc; and so on.

In case that the present pesticidal composition is lotion, spot-on formulation, pour-on formulation or shampoo, it is applied to animals by itself. Dusts and aerosol formulations may be applied to animals directly or applied to animals living quarters, their surroundings the places pest inhabits, and so on. Collars or ear-tags are used by setting them to animals.

In the present pesticidal method using an insect growth regulating compound and carane-3,4-diol together, it is convenient to use the pesticidal composition of the present invention containing both ingredients. However, there is no need to prepare the pesticidal composition of the present invention containing both ingredients in advance and use it. It may be used a formulation containing an insect growth regulating compound and another formulation containing carane-3,4-diol at the same time.

EXAMPLES

The following examples further illustrate the present invention in detail.

The formulation examples of the present pesticidal composition are shown below.

Formulation Example 1

Pyriproxyfen (0.05 part by weight) and 1S,3S,4S,6R-carane-3,4-diol (5 parts by weight) are solved to ethanol to be 35 parts by weight in total and the solution is poured into an aerosol container. Next, a valve is added to the container and LPG (propellant, 65 parts by weight) is charged in the container through the valve part under pressure to give an aerosol formulation.

Formulation Example 2

Pyriproxyfen (5 parts by weight), 1S,3S,4S,6R-carane-3,4-diol (50 parts by weight) and permethrin (45 parts by weight) are mixed to give a spot-on formulation.

Formulation Example 3

Methoprene (3 parts by weight), 1S,3S,4S,6R-carane-3,4-diol (47 parts by weight) and dipropylene glycol monomethyl ether (50 parts by weight) are mixed to give a spot-on formulation.

Formulation Example 4

A support layer of Kuralino 6038-0018 (artificial leather material), manufactured by Kuraray Co., Ltd. , having a length of 35.8 cm, a width of 1.5 cm and a thickness of 0.28 cm, was impregnated with pyriproxyfen (0.01 g) and 1S,3S,4S,6R-carane-3,4-diol (2.0 g) by adding them dropwise to the surface of the support layer, and one tip of the resulting material is equipped with a buckle to prepare a collar.

Next, effectiveness of the present pesticidal method is shown in the following test example.

Test Example 1

Each of pyriproxyfen, 1S,3S,4S,6R-carane-3,4-diol and a mixture thereof was diluted with acetone, added dropwise to a filter paper (3.8 cm in diameter) and dried. About 20 eggs (within 24 hours after laid) of cat flea were set on the filter paper prepared above. The filter paper was held in a plastic plate, kept 26° C. of temperature and 95% of humidity for 5 days and hatching was observed. The tests were repeated 3 times and the results are shown in Table 1.

Hatching inhibition ratio (%) in Table represents a corrected inhibition ratio (%) which is calculated by the following:

$$\text{Hatching inhibition ratio (\%)} = \{(C-T)/C\} \times 100$$

wherein C is a hatching ratio (92.4%) of flea at non-treated area and T is a hatching ratio of flea at treated area.

In the table, PY means pyriproxyfen and CA means 1S,3S,4S,6R-carane-3,4-diol. The treated dosage unit is mg/m$^2$.

TABLE 1

| Ingredient | treated dosage (mg/m$^2$) | Hatching inhibition ratio (%) |
|---|---|---|
| PY + CA | 0.1 + 1.0 | 78.4 |
| PY + CA | 0.1 + 100 | 84.0 |
| PY | 0.1 | 58.1 |
| CA | 10 | 3.1 |
| CA | 100 | 12.1 |

The hatching inhibition activity of pyriproxyfen (insect growth regulating compound) against flea eggs is highly increased by an addition of carane-3,4-diol as shown in the table.

I claim:

1. A pesticidal composition which comprises an insect growth regulating compound and carane-3,4-diol as active ingredients, and an inert carrier.

2. The pesticidal composition according to claim 1, wherein the weight ratio of an insect growth regulating compound and carane-3,4-diol is within the range of 1:3 to 1:5000.

3. The pesticidal composition according to claim 2, wherein the insect growth regulating compound is at least one selected from the group consisting of pyriproxyfen, methoprene, fenoxycarb, chlorfluazuron, hexaflumuron, lufenuron, teflubenzuron, flufenoxuron, N-2,6-difluorobenzoyl-N'-[2-fluoro-4-(1,1,2,3,3,3-hexafluoropropoxy)phenyl]urea and N-2,6-difluorobenzoyl-N'-[2-fluoro-4-(1,1,2,2-tetrafluoroethyoxy)phenyl]urea.

4. The pesticidal composition according to claim 2, wherein the insect growth regulating compound is pyriproxyfen.

5. The pesticidal composition according to claim 1, wherein the weight ratio of an insect growth regulating compound and carane-3,4-diol is within the range of 1:10 to 1:1000.

6. The pesticidal composition according to claim 5, wherein the insect growth regulating compound is at least one selected from the group consisting of pyriproxyfen, methoprene, fenoxycarb, chlorfluazuron, hexaflumuron, lufenuron, teflubenzuron, flufenoxuron, N-2,6-difluorobenzoyl-N'-[2-fluoro-4-(1,1,2,3,3,3-hexafluoropropoxy)phenyl]urea and N-2,6-difluorobenzoyl-N'-[2-fluoro-4-(1,1,2,2-tetrafluoroethyoxy)phenyl]urea.

7. The pesticidal composition according to claim 5, wherein the insect growth regulating compound is pyriproxyfen.

8. The pesticidal composition according to claim 1, wherein the insect growth regulating compound is at least one selected from the group consisting of pyriproxyfen, methoprene, fenoxycarb, chlorfluazuron, hexaflumuron, lufenuron, teflubenzuron, flufenoxuron, N-2,6-difluorobenzoyl-N'-[2-fluoro-4-(1,1,2,3,3,3-hexafluoropropoxy)phenyl]urea and N-2,6-difluorobenzoyl-N'-[2-fluoro-4-(1,1,2,2-tetrafluoroethoxy)phenyl]urea.

9. The pesticidal composition according to claim 1, wherein the insect growth regulating compound is pyriproxyfen.

10. A method of controlling pests which comprises using an insect growth regulating compound and carane-3,4-diol together.

11. A method for controlling hatching of flea eggs which comprises using an insect growth regulating compound and carane-3,4-diol together.

12. A method of controlling fleas which comprises applying an insect growth regulating compound and carane-3,4-diol together to animals.

* * * * *